US005723692A

United States Patent [19]

Clement et al.

[11] Patent Number: 5,723,692
[45] Date of Patent: Mar. 3, 1998

[54] PREPARATION OF 4,4'-DIHYDROXY-'ALKYLSTIBLBENE WITH REDUCED DIMER FORMATION

[75] Inventors: Katherine S. Clement; Robert E. Hefner, Jr.; Emmett L. Tasset, all of Lake Jackson; Louis L. Walker, Clute, all of Tex.

[73] Assignee: The Dow Chemical Company, Midland, Mich.

[21] Appl. No.: 713,330

[22] Filed: Sep. 13, 1996

[51] Int. Cl.[6] .................................................. C07C 39/215
[52] U.S. Cl. ............................................................ 568/729
[58] Field of Search ................................................ 568/729

[56] References Cited

U.S. PATENT DOCUMENTS

| | | |
|---|---|---|
| 2,623,908 | 12/1952 | Stoesser et al. . |
| 3,221,061 | 11/1965 | Grover et al. . |
| 3,326,986 | 6/1967 | Dungan et al. . |
| 3,624,162 | 11/1971 | Sieber ........................... 260/619 B |
| 5,414,150 | 5/1995 | Hefner, Jr. et al. . |
| 5,463,091 | 10/1995 | Earls et al. . |
| 5,475,155 | 12/1995 | Hefner et al. ........................ 568/727 |

FOREIGN PATENT DOCUMENTS 949668  2/1964  United Kingdom .

OTHER PUBLICATIONS

Harrison, I. T., Journal of the Chemical Society, Chemical Communications, p. 616 (1969).

Kawasaki, I. et al., Bulletin of the Chemical Society of Japan, vol. 44, pp. 1986–1987 (1971).

McOmie, J. F. W. et al., Tetrahedron, vol. 24 pp. 2289–2292 (1968).

Percec, V. et al., Mol. Cryst. Liq. Cryst., vol. 205, pp. 47–66 (1991).

Zaheer, S. H. et al., Journal of the Chemical Society, Part 1, pp. 3360–3362 (1954).

US Patent Application entitled, "Process for the Preparation and Purification of 4,4'-Dihydroxy-αSubstituted Stilbene" filed Feb. 29, 1996; Serial No. 08/608,807; Applicants: A. P. Haag et al.

*Primary Examiner*—S. Mark Clardy
*Assistant Examiner*—Barbara Badio
*Attorney, Agent, or Firm*—Reid S. Willis

[57] ABSTRACT

Preparation of dihydroxy-α-alkylstilbenes with reduced undesirable by-products can be achieved by carrying out dehydrohalogenation of a substantially uniform dispersion of a halogenated intermediate of the desired product in the presence of water and a polar protic solvent.

20 Claims, No Drawings

PREPARATION OF 4,4'-DIHYDROXY-'ALKYLSTIBLBENE WITH REDUCED DIMER FORMATION

BACKGROUND OF THE INVENTION

Dihydroxy-α-alkylstilbenes, which are useful as precursors to thermotropic thermosets and thermoplastics, are generally prepared by the condensation of an α-haloketone and a phenolic compound to form a halogenated intermediate, followed by dehydrohalogenation of the intermediate. One such preparation (Zaheer et al., *J. Am. Chem. Soc.*, Part 3, pp. 3360–3362 (1954)) discloses the dropwise addition of concentrated sulfuric acid to a solution of phenol and chloroacetone maintained at −10° C. for 2 to 3 hours, with the mole ratio of acid to phenol to chloroacetone to sulfuric acid being 0.3:0.6:0.3. The product is washed with water, then crystallized from hot aqueous ethanol, washed with light petroleum, recrystallized twice in ethanol and once in benzene to obtain the desired product, 4,4'-dihydroxy-α-methylstilbene (DHAMS), at a yield of 66.4 percent. The melting point of the 3-times recrystallized product was reported to be 182° C. 183° C., or 5 to 6 degrees lower than the melting point for the pure product.

Another preparation of DHAMS is described by Percec, et al. in *Mol. Cryst. Liq. Cryst.*, Vol. 205, pp. 47–66 (1991). In this example, sulfuric acid is added to a solution of phenol and chloroacetone using a mole ratio of acid to phenol to chloroacetone of 2.0:0.995:0.47. A 5.9 percent yield of DHAMS having a purity of 99.6 to 99.9 percent was obtained after six recrystallizations from ethanol and water.

Multiple recrystallizations are often required to obtain over 99 percent purity of the desired product because of the formation of difficult-to-separate by-products. It would therefore be an advance in the field to discover a process of preparing a dihydroxy-α-alkylstilbene which produced lower yields of these by-products.

SUMMARY OF THE INVENTION

The present invention is a process of preparing a 4,4'-dihydroxy-α-alkylstilbene comprising the steps of:

a) contacting under dehydrohalogenation conditions a halogenated intermediate and optionally a water-immiscible solvent with a solution containing water and a polar protic solvent, wherein:
   i) the volume-to-volume ratio of the polar protic solvent to the water is not less than 1:2;
   ii) the concentration of the halogenated intermediate does not exceed 30 gs per 100 mL of the water, the water-immiscible solvent, and the polar protic solvent; and
   iii) the halogenated intermediate is prepared by the acid catalyzed condensation of a phenolic compound and an α-haloketone; and b) increasing the concentration of water with respect to the polar protic solvent to precipitate the 4,4'-dihydroxy-α-alkylstilbene.

In another aspect, the present invention is a process for preparing a 4,4'-dihydroxy-α-alkylstilbene comprising the steps of:

a) adding under dehydrohalogenation conditions a mixture containing a halogenated intermediate, a water-immiscible solvent, and a phenolic compound, to a solution containing water and a polar protic solvent, wherein:

i) the concentration of the halogenated intermediate in the water, the water-immiscible solvent, and the polar protic solvent;
   ii) the volume-to-volume ratio of the polar protic solvent to water; and
   iii) the polar protic solvent;

are all selected so that the yield of the total dimers of the α-alkylstilbene does not exceed 3 percent at a complete conversion of the halogenated intermediate, the halogenated intermediate being prepared by the acid-catalyzed condensation of a phenolic compound and an α-haloketone; and b) increasing the concentration of water with respect to the polar protic solvent to precipitate the 4,4'-dihydroxy-α-alkylstilbene.

In a further aspect, the present invention is a method of increasing the ratio of a trans-to a cis-α-alkylstilbene in a mixture containing the trans- and the cis-α-alkylstilbenes, a phenolic compound and water, comprising the step of distilling an azeotrope of the water and the phenolic compound, wherein the amount of water present in the mixture after distillation is sufficient to form an aqueous slurry of the α-alkylstilbenes that is enriched in the transisomer and reduced in the phenol.

It has been surprisingly discovered that yields and purity of the 4,4'-dihydroxy-α-alkylstilbene are improved, and the formation of undesirable dimers are diminished using the process of the present invention.

DETAILED DESCRIPTION OF THE INVENTION

The term "halogenated intermediate" is used herein to describe a compound which is an acid catalyzed condensation product of an α-haloketone and a phenolic compound.

The halogenated intermediate can be prepared by reacting a stoichiometric excess of a phenolic compound with an α-haloketone and a strong acid. Phenolic compounds suitable for the preparation of the halogenated intermediate include those compounds disclosed by Hefner, Jr. et al. in U.S. Pat. No. 5,475,155 (hereinafter "Hefner"), column 4, line 64 to column 5, line 28. Suitable α-haloketones include those disclosed by Hefner, column 5, line 65 to column 6, line 27; and suitable strong acids include those disclosed by Hefner, column 6, lines 46–64, all of which disclosures are incorporated herein by reference. Phenol is the most preferred phenolic compound; chloroacetone is the most preferred α-haloketone; and concentrated sulfuric acid and methanesulfonic acid are the most preferred strong acids.

The mole-to-mole ratio of the phenolic compound to the α-haloketone is preferably not less than about 2:1, more preferably not less than about 2.5:1, and most preferably not less than 3:1; and preferably not more than about 15:1, more preferably not more than about 8:1, and most preferably not more than about 5:1. The mole-to-mole ratio of the strong acid to the phenolic compound is preferably not less than about 0.1:1, more preferably not less than 0.5:1, and most preferably not less than 1:1; and preferably not more than 10:1, more preferably not more than 5:1, and most preferably not more than 3:1.

Although the halogenated intermediate may be prepared by adding the strong acid to a mixture of the phenolic compound and the α-haloketone, the α-haloketone may also be added gradually (for example, dropwise over an hour) to a mixture containing the phenolic compound and the strong acid, preferably sulfuric acid or methanesulfonic acid. The reaction is preferably carried out at a temperature not less than −25° C., more preferably not less than −20° C., and most preferably not less than −15° C.; and preferably not more than 15° C., more preferably not more than 5° C., and most preferably not more than −5° C.

The reaction to form the halogenated intermediate may be carried out in the presence of a water-immiscible solvent. The term "water-immiscible solvent" is used herein to refer to a solvent that is not more than 10 percent, preferably not more than 5 percent, and most preferably not more than 3 percent soluble in water at 20° C. Such solvents include methylene chloride, chloroform, carbon tetrachloride, 1,2-dichloroethane, 1,1-dichloroethane, 1,1,1-trichloroethane, 1,1,2-trichloroethane, fluorotrichloromethane, and bromotrichloromethane, with methylene chloride and chloroform being more preferred, and methylene chloride being most preferred.

Although the α-haloketone may serve as a solvent or cosolvent, it is not a preferred solvent. In the special case where the α-haloketone is used as a solvent or cosolvent, the mole ratio of phenol:α-haloketone is preferably in the range of about 0.1:1 to 1.99:1. However, the amount of α-haloketone present in the solution containing the halogenated intermediate just prior to dehydrohalogenation is preferably not more than 5, more preferably not more than 1, most preferably not more than 0.5 volume percent of the solvents in the solution.

The amount of the water-immiscible solvent used is dependent upon the nature of the reagents, and more critically dependent on the mode of addition of the reagents. For example, when the α-haloketone is slowly added to the mixture containing the phenolic compound and the strong acid, less water-immiscible solvent is required to keep the reaction mixture from freezing at temperatures less than 0° C. than when acid is added to a mixture containing the α-haloketone and the phenolic compound. The minimization of the water-immiscible solvent in the step to form the halogenated intermediate is desirable because the condensation-reaction-kinetics to form the desired intermediate are improved, and the formation of undesirable trisphenolic by-products are diminished.

After a desired amount of the halogenated intermediate is formed (as determined, for example, by monitoring the reaction by liquid chromatography), the halogenated intermediate is preferably not isolated. Instead, acids are advantageously removed by first quenching the reaction with cold water (about 0° C. to about 5° C.) and a cold, water-immiscible solvent to form a biphasic mixture, then separating the aqueous phase from the phase that contains the chlorinated intermediate. The biphasic mixture, more particularly the phase that contains the chlorinated intermediate, the unreacted phenol, and optionally the water-immiscible solvent, is advantageously maintained at a temperature sufficiently low to prevent substantial decomposition or reaction of the intermediate, preferably not less than −25° C., more preferably not less than −20° C., and most preferably not less than −15° C., and preferably not more than 15° C., more preferably not more than 5° C., and most preferably not more than −5° C. Maintenance of the chlorinated intermediate phase at these sufficiently low temperatures is desired until this phase is contacted with a polar protic solvent and water as described hereinbelow.

The chlorinated intermediate phase is preferably washed a sufficient number of times with cold water to remove substantially all the acid from the phase so that the acid is present at a concentration of not more than 10,000 ppm, preferably not more than 5000 ppm, more preferably not more than 1000 ppm, and most preferably not more than 100 ppm. If a water-immiscible solvent is present in the chlorinated intermediate phase, it is preferably not removed for the subsequent dehydrohalogenation reaction. The chlorinated intermediate phase is preferably not contacted with a drying agent to remove residual water.

In one aspect of the process of the present invention, the phase containing the halogenated intermediate is contacted with water and a polar protic solvent wherein the volume-to-volume ratio of the polar protic solvent to the water is not less than 1:2. The polar protic solvent is used in a sufficient amount to form a substantially uniform dispersion of the components, preferably throughout the course of the conversion of the halogenated intermediate. The term "substantially uniform dispersion" is used herein to refer to a mixture wherein at least about 90 weight percent, more preferably at least about 95 percent, of the components are in a single phase. Similarly, the term "uniform dispersion" is used herein to refer to a mixture wherein all of the components form a single phase.

Examples of suitable polar protic solvents include alcohols or glycols such as methanol, ethanol, n-propanol, isopropanol, n-butanol, isobutanol, t-butanol, t-amyl alcohol, ethylene glycol, ethylene glycol monomethyl ether, ethylene glycol monoethyl ether, propylene glycol monomethyl ether, and diethylene glycol monomethyl ether. More preferred polar protic solvents include ethanol, isopropanol, and t-butanol, with isopropanol and t-butanol being most preferred.

The volume-to-volume ratio of the polar protic solvent to the water is, of course, application dependent as well as dependent on the nature of polar protic solvent, but is preferably not less than 1:1, more preferably not less than 2:1, and most preferably not less than 4:1; and preferably not more than 500:1, more preferably not more than 50:1, and most preferably not more than 20:1.

The volume percent of the water-immiscible solvent present in the reaction mixture after contact of the halogenated intermediate with the solution containing the water and polar protic solvent is preferably not greater than 50, more preferably not greater than 20, and most preferably not greater than 10 volume percent; and preferably not less than 0.5, more preferably not less than 1, and most preferably not less than 5 volume percent based on the volume of the polar protic solvent, the water, and the water-immiscible solvent.

The concentration of the chlorinated intermediate in the solvents is highly dependent on the nature of the polar protic solvent as well as the ratio of the polar protic solvent to water, but is preferably not more than 30 g, more preferably not more than 20 g, still more preferably not more than 15 g, and most preferably not more than 10 g per 100 mL of total solvent (that is, the polar protic solvent, the water, and the water-immiscible solvent).

The chlorinated intermediate phase, which is preferably substantially acid free and also contains unreacted phenolic compound and the water-immiscible solvent, is contacted with the water and polar protic solvent under conditions suitable to promote dehydrohalogenation. Although the reaction can occur at about 25° C. or below, it is preferable to carry out the reaction at a temperature not less than about 40° C., more preferably not less than about 60° C., and most preferably not less than about 75° C., and preferably not more 150° C., more preferably not more than 125° C., most preferably not more than 100° C.

It may be desirable in some instances to add the cold, substantially acid-free chlorinated intermediate phase gradually to a preheated solution containing water and the polar protic solvent, more preferably to a solution containing the water and the isopropanol or t-butanol that is maintained in a temperature range of not less than 60° C. and not more than 85° C., so that the effective dilution of the halogenated intermediate in the water and the polar protic solvent is increased. For example, the addition of 30 g of halogenated intermediate over the course of an hour into 100 mL of hot alcohol and water can effectively reduce the concentration of the halogenated intermediate to substantially less than 30 g/100 mL since dehydrohalogenation to the desired product usually occurs during the course of the slow addition. It is most preferred that the reaction mixture remain monophasic throughout the the course of the reaction. If desired, the course of the reaction can be monitored, for example, by liquid chromatography.

Under the most preferred dehydrohalogenation conditions, the water-immiscible solvent, if present, is removed during the course of the dehydrohalogenation reaction. It may also be desirable in some instances to buffer the hydrogen halide that is liberated by adding base, preferably at sufficiently low enough amounts to ensure that the reaction mixture does not become basic during the course of the dehydrohalogenation reaction.

When substantial conversion of the halogenated intermediate is achieved, preferably at least 90 percent, more preferably at least 95 percent, and most preferably at least 99 percent conversion, as monitored, for example, by liquid chromatography, the concentration of water with respect to the polar protic solvent is increased to precipitate the dihydroxy-α-alkylstilbene. This increase in concentration can be achieved by contacting the reaction mixture with sufficient water, or by the removal of sufficient polar protic solvent, for example, by evaporation or in vacuo distillation, to precipitate or crystallize the dihydroxy-α-alkylstilbene.

It has also been surprisingly discovered that the ratio of the trans- to the cis-isomer of the dihydroxy-α-alkylstilbene can be increased by the azeotropic removal of phenol, preferably in vacuo and at elevated temperature, in the presence of a sufficient amount of water to form a slurry of water and the dihydroxy-α-alkylstilbene that is more highly concentrated with the preferred trans-isomer.

The reaction mixture may also be contacted with water and a sufficient amount of base to neutralize the solution and promote precipitation of the dihydroxy-α-alkylstilbene. Preferred bases include sodium bicarbonate, potassium bicarbonate, potassium hydroxide, and sodium hydroxide. The desired product can then be filtered off, and an organic phase which may be present in the filtrate may be separated from the aqueous phase and processed further to recover additional dihydroxy-α-alkylstilbene.

If further purification of the dihydroxy-α-alkylstilbene is desired, the product may be recrystallized, preferably in a mixture of a $C_1$–$C_3$ alcohol and water, more preferably in about a 40:60 to about 60:40 volume-to-volume mixture of isopropanol or ethanol and water, and most preferably in about a 50:50 volume-to-volume mixture of isopropanol and water. The ratio of recrystallizing solvent to the dihydroxy-α-alkylstilbene is preferably not less than about 1:1, more preferably not less than about 2:1, most preferably not less than about 2.5:1, and not more than about 10:1, more preferably not more than 6:1, and most preferably not more than 4:1.

The dehydrohalogenation process of the present invention may conveniently be run using a batch process, as described hereinabove, or a continuous process, which may involve countercurrent flow of a stream of the washed condensation reaction product into a heated solution of polar protic solvent and water confined within a tubular reactor configuration. Alternatively, a series of stirred tank reactors may be used in a continuous process.

It has surprisingly been discovered that the selectivity of the reaction to the formation of the desired dihydroxy-α-alkylstilbene product is increased, and the amount of undesirable dimers such as cis- and trans-1,2,4,5-tetrakis(4-hydroxyphenyl)-4-pentenes are significantly reduced when the dehydrohalogenation reaction is carried out as described herein. The yield of undesirable dimers formed in the crude dehydrohalogenation product (that is, prior to recrystallization) at complete conversion of the halogenated intermediate is preferably not more than about 5 percent, more preferably not more than about 3 percent, and still more preferably not more than 1 percent, and most preferably not more than 0.5 percent. This reduction in dimer formation is significant because of the difficulty in separating these dimers from the desired product, the dihydroxy-α-alkylstilbene. Thus, a single recrystallization of the crude product prepared by the process of the present invention is ordinarily sufficient, preferably unnecessary, to obtain a purity of at least 99 percent using the process of the present invention.

The following examples are for illustrative purposes only and are not intended to limit the scope of this invention. All percentages are by weight unless otherwise noted.

EXAMPLE 1

Preparation of 4,4'-Dihydroxy-α-methylstilbene (DHAMS) Using Methanesulfonic Acid Into a jacketed flask fitted with a nitrogen inlet and outlet, an addition funnel, a thermometer, and an overhead stirrer is added methanesulfonic acid (192.2 g, 2 mol), phenol (107.55 g, 1.14 mol), and methylene chloride (10 g). The flask is cooled to less than –15° C. whereupon chloroacetone (27.83 g, 0.2857 mol) is added dropwise along with 2 mL of methylene chloride rinses. The temperature is adjusted to –10° C. to –12° C., and stirring is continued until gas chromatographic analysis of an aliquot of the mixture shows the chloroacetone peak to be less than 1 percent by area of the chlorinated intermediate peak. The mixture is cooled to –15° C., whereupon 100 g of cold methylene chloride (–20° C.), then 283 g of chilled water (0° C. to 5° C.) are added to form a biphasic mixture. The mixture is agitated and the temperature of the solution is raised to 0° C. Agitation is ceased, and the lower (organic) layer is drained off and poured into a flask containing water (358.2 g) and isopropanol (716 g, 910 mL) maintained at 65° C. The total concentration is at most 0.42 moles chlorinated intermediate per liter of water, isopropanol, and methylene chloride, (5.5 g/100 mL) assuming 100 percent conversion to chlorinated intermediate. The mixture is stirred under nitrogen for 3½ hours, then neutralized by 40 g of 30 percent NaOH (aqueous). The mixture is concentrated by rotary evaporation to remove essentially all of the isopropanol, thereby causing large crystals to precipitate. The crystals are washed with methylene chloride followed by hot water (greater than 80° C.), then dried in a vacuum oven at 60° C. to 80° C. The yield of the product is 50.45 g (78 percent) with a purity of 99.23 percent. The total yield of 1,2,4,5-tetrakis(4-hydroxyphenyl)-4-pentenes is less than 0.4 percent.

EXAMPLE 2

Preparation of DHAMS Using Sulfuric Acid

To a 5-liter glass reactor equipped with a chilled ethylene glycol-water condenser (–5° C.), mechanical stirrer, nitrogen purge, thermometer, dropping funnel, and jacket for circulating coolant over the reactor exterior are added phenol (1411.5 g, 15.0 moles), chloroacetone (95.5 g, containing 96.9 percent chloroacetone (1.0 mole), 2.75 percent 1,1-dichloroacetone, 0.30 percent mesityl oxide and 0.05 percent acetone) and methylene chloride (2650 g, 2 L). The reactor is cooled to −10° C. and stirring is commenced, at which time concentrated sulfuric acid (196.2 g, 2.0 moles) is added dropwise to the stirred reaction mixture over 60 minutes, over which time the reaction temperature is maintained at between −10° C. and −12° C. After 41 hours and 16 minutes of stirring, an aliquot of the reaction mixture is analyzed and found to contain undetectable levels (less than 0.01 percent) of chloroacetone. Chilled deionized water (7° C.) is added to the reaction mixture, forming an aqueous phase and an organic portion, while raising the temperature to −7° C. The organic portion is washed 5 times (450- to 550-mL washes), then separated into 3 equal portions of 1263 g each (0.333 g maximum of halogenated intermediate). Each portion is added dropwise over 30 minutes into 3 separate reaction vessels containing magnetically stirred water (200 g) and ethanol (1200 g, 1520 mL) and placed on a hot plate that controlled the temperature at 82° C. The addition of the solution containing the halogenated intermediate is controlled to maintain a temperature between 72° C. and 82° C. The maximum concentration of halogenated intermediate in the total solvents (methylene chloride, water, and ethanol) in each vessel is 0.14 moles/L (1.8 g/100 mL). After completion of the addition, each vessel is removed from the heat source and allowed to cool for 6.5 hours, at which time the temperature is about 25° C. Sodium bicarbonate (40 g) is added to each vessel over 5 minutes. The mixtures are stirred for 16.75 hours, whereupon the contents are combined and split into two flasks (2268.5 g each). Sodium bicarbonate (40 g) is added to each flask, and the volatiles are removed by rotary evaporation (75° C. to 82° C. at 1 mm Hg) to yield a total of 867 g. The portions are combined and added to water (2 L) to form a slurry. The slurry is stirred for 17 hours, after which time the crystalline product is recovered by vacuum filtration. The wet cake is then combined with water (450 mL) and the slurry is heated with stirring to 100° C. for one minute. The slurry is then filtered through a coarse fritted glass filter, and the crystalline product cake is washed with an additional 200 mL of boiling water. The product is then dried in a vacuum oven at 80° C. and 1 mm Hg to yield 137 g (60.6 percent yield) of crystalline product. HPLC analysis of a portion of the product shows 98.0 weight percent (normalized) trans-4,4'-dihydroxy-α-methylstilbene, 0.5 percent cis-4,4'-dihydroxy-α-methylstilbene, and less than 0.2 weight percent of the total dimers cis- and trans-1,2,4,5tetrakis(4-hydroxyphenyl)-4-pentenes.

What is claimed is:

1. A process of preparing a 4,4'-dihydroxy-α-alkylstilbene comprising the steps of:
   a) contacting under dehydrohalogenation conditions a halogenated intermediate and optionally a water-immiscible solvent with a solution containing water and a polar protic solvent to form a substantially uniform dispersion, wherein:
      i) the volume-to-volume ratio of the polar protic solvent to the water is not less than 1:2;
      ii) the concentration of the halogenated intermediate does not exceed 30 gs per 100 mL of the water, the water-immiscible solvent, and the polar protic solvent; and
      iii) the halogenated intermediate is prepared by the acid catalyzed condensation of a phenolic compound and an α-haloketone; and
   b) increasing the concentration of water with respect to the polar protic solvent to precipitate the 4,4'-dihydroxy-α-alkylstilbene.

2. The process of claim 1 wherein the polar protic solvent is methanol, ethanol, n-propanol, isopropanol, n-butanol, isobutanol, t-butanol, t-amyl alcohol, ethylene glycol, ethylene glycol monomethyl ether, ethylene glycol monoethyl ether, propylene glycol monomethyl ether, or diethylene glycol monomethyl ether or a combination thereof, and wherein the volume-to-volume ratio of the polar protic solvent to the water is not less than 1:1 and not greater than 500:1.

3. The process of claim 2 wherein the polar protic solvent is isopropanol or t-butanol, or a combination thereof.

4. The process of claim 3 wherein the volume-to-volume ratio of the polar protic solvent to water is not less than 2:1, and the concentration of the halogenated intermediate is sufficiently low such that the yield of total dimers of the dihydroxy-α-methylstilbene formed in a crude dehydrohalogenated product is not more than 3 percent.

5. The process of claim 3 wherein the halogenated intermediate is prepared by reacting phenol with chloroacetone in the presence of sulfuric acid or methanesulfonic acid.

6. The process of claim 5 wherein the volume-to-volume ratio of the polar protic solvent to water is not less than 4:1, and the concentration of the halogenated intermediate is sufficiently low such that the yield of 1,2,4,5-tetrakis(4-hydroxyphenyl)-4-pentenes does not exceed about 0.5 percent at a complete conversion of the halogenated intermediate.

7. The process of claim 5 wherein the mole ratio of the phenolic compound to the α-haloketone is not less than about 3:1 and not more than about 5:1.

8. The process of claim 7 wherein the mole ratio of the acid to the phenolic compound is not less than about 1:1 and not more than about 3:1.

9. The process of claim 5 wherein the halogenated intermediate is prepared by adding the sulfuric acid or methanesulfonic acid or a combination thereof to a mixture containing the phenolic compound and the α-haloketone.

10. The process of claim 1 wherein the halogenated intermediate and the water-immiscible solvent is added gradually to a preheated solution containing the water and the polar protic solvent, so as to increase the effective dilution of the halogenated intermediate in the water and the polar protic solvent.

11. The process of claim 1 wherein the concentration of the halogenated intermediate is not greater than about 15 gs per 100 mL of the water, the water-immiscible solvent, and the polar protic solvent.

12. The process of claim 1 wherein the water-immiscible solvent is present at a concentration of not greater than 20 volume percent based on the volume of the polar protic solvent, the water, and the water-immiscible solvent, and further that the water immiscible solvent is methylene chloride, chloroform, carbon tetrachloride, 1,2-dichloroethane, 1,1-dichloroethane, 1,1,1-trichloroethane, bromotrichloromethane, fluorotrichloromethane, or 1,1,2-trichloroethane, or a combination thereof.

13. The process of claim 12 wherein the water-immiscible solvent is methylene chloride or chloroform.

14. The process of claim 1 which forms a uniform dispersion throughout the course of the dehydrohalogenation.

15. The process of claim 1 wherein in step (b) the concentration of water with respect to the polar protic solvent is increased by removal of at least a portion of the polar protic solvent.

16. A process for preparing a 4,4α-dihydroxy-α-alkylstilbene comprising the steps of:
 a) adding under dehydrohalogenation conditions a mixture containing a halogenated intermediate, a water-immiscible solvent, and a phenolic compound, to a solution containing water and a polar protic solvent, wherein:
  i) the concentration of the halogenated intermediate in the water, the water-immiscible solvent, and the polar protic solvent;
  ii) the volume-to-volume ratio of the polar protic solvent to water; and
  iii) the polar protic solvent;
 are all selected so that the yield of the total dimers of the α-alkylstilbene does not exceed 3 percent at a substantially complete conversion of the halogenated intermediate, the halogenated intermediate being prepared by the acid-catalyzed condensation of a phenolic compound and an α-haloketone; and
 b) increasing the concentration of water with respect to the polar protic solvent to precipitate the 4,4'-dihydroxy-α-alkylstilbene.

17. The process of claim 16 wherein in step (a):
 i) the mixture containing the halogenated intermediate, the water-immiscible solvent, and the phenolic compound is maintained at a temperature in the range of about 5° C. to about −20° C. before being added to the solution containing the water and the polar protic solvent;
 ii) the temperature of the solution containing the water and the polar protic solvent is in the range of about 60° C. to about 85° C. before and after the addition thereto of the mixture containing the halogenated intermediate, the water-immiscible solvent, and the phenolic compound;
 iii) a uniform dispersion is maintained throughout the course of the dehydrohalogenation;
 iv) the water-immiscible solvent is removed from the mixture during the course of dehydrohalogenation;
 v) the polar protic solvent is a $C_1$–$C_5$ alcohol;
 vi) the volume-to-volume ratio of the polar protic solvent is not less than 2:1;
 vii) the concentration of the halogenated intermediate does not exceed 15 g per 100 mL of the water, the water-immiscible solvent, and the polar protic solvent;
 viii) the phenolic compound is phenol; and
 ix) the yield of total dimers of the α-alkylstilbene does not exceed 1 percent at a complete conversion of the halogenated intermediate.

18. The process of claim 17 wherein the concentration of water with respect to the $C_1$–$C_5$ alcohol is increased by evaporation or in vacuo distillation of the alcohol, wherein the $C_1$–$C_5$ alcohol is isopropanol or t-butanol.

19. The process of claim 18 wherein an azeotropic mixture of phenol and water are removed so as to form a slurry of the 4,4'-dihydroxy-α-alkylstilbene which is more highly enriched with the trans-isomer of the 4,4'-dihydroxy-α-alkylstilbene.

20. A method of increasing the ratio of a trans- to a cis-α-alkylstilbene in a mixture containing the trans- and the cis-α-alkylstilbenes, a phenolic compound, and water, comprising the step of distilling an azeotrope of the water and the phenolic compound, wherein the amount of water present in the mixture after distillation is sufficient to form an aqueous slurry of the α-alkylstilbenes that is enriched in the trans-isomer and reduced in the phenol.

* * * * *